United States Patent
Brooks et al.

(10) Patent No.: US 9,680,333 B1
(45) Date of Patent: Jun. 13, 2017

(54) POWER SYSTEM FOR A MEDICAL CART WITH A DIRECT CURRENT POWER BUS

(71) Applicant: Capsa Solutions, LLC, Portland, OR (US)

(72) Inventors: Richard Jason Brooks, Huntersville, NC (US); Derek J. Nash, Greer, SC (US)

(73) Assignee: CAPSA SOLUTIONS, LLC, Portland, OR (US)

( * ) Notice: Subject to any disclaimer, the term of this patent is extended or adjusted under 35 U.S.C. 154(b) by 870 days.

(21) Appl. No.: 13/840,318

(22) Filed: Mar. 15, 2013

(51) Int. Cl.
H02J 9/06 (2006.01)
H02H 3/00 (2006.01)
H02J 7/00 (2006.01)

(52) U.S. Cl.
CPC ............ *H02J 9/06* (2013.01); *H02H 3/00* (2013.01); *H02J 7/0042* (2013.01); *Y10T 307/625* (2015.04)

(58) Field of Classification Search
CPC ..... H02J 9/06; Y10T 307/615; Y10T 307/625
USPC ............................... 307/64, 66, 150
See application file for complete search history.

(56) References Cited

U.S. PATENT DOCUMENTS

| | | | | |
|---|---|---|---|---|
| 5,695,886 A * | 12/1997 | Dewan | ............... | H01M 10/46 320/106 |
| 5,721,481 A * | 2/1998 | Narita | ............... | H02J 7/0013 307/46 |
| 2007/0055116 A1 * | 3/2007 | Clark | ............... | A61B 5/0002 600/300 |
| 2007/0228680 A1 * | 10/2007 | Reppert | ............... | A47B 21/00 280/47.35 |
| 2012/0203377 A1 * | 8/2012 | Paydar | ............... | G01K 3/005 700/232 |
| 2012/0281817 A1 * | 11/2012 | McBroom | ............... | A61B 6/56 378/204 |
| 2013/0093242 A1 * | 4/2013 | Mok | ............... | H02J 9/005 307/23 |
| 2013/0200579 A1 * | 8/2013 | Abernethy | ............... | B62B 3/02 280/6.15 |
| 2014/0265193 A1 * | 9/2014 | Stark | ............... | B62B 3/10 280/47.34 |
| 2015/0227127 A1 * | 8/2015 | Miller | ............... | G05B 19/042 700/244 |

* cited by examiner

Primary Examiner — Fritz M Fleming
(74) Attorney, Agent, or Firm — Standley Law Group LLP

(57) ABSTRACT

A power system for a medical cart includes a power supply, a direct current power bus electrically coupled to the power supply, and an electrical output power module electrically coupled to the direct current power bus. The power supply is positioned within the base of the medical cart and outputs direct current electrical power. The direct current power bus is the support of the medical cart, with the base being at one end of the support. The electrical output power module is within the work platform of the medical cart at the other end of the support. The electrical output power module inputs the direct current electrical power from the direct current power bus, and converts the input direct current electrical power to an electrical power output having a different state.

20 Claims, 10 Drawing Sheets

US 9,680,333 B1

POWER SYSTEM FOR A MEDICAL CART WITH A DIRECT CURRENT POWER BUS

TECHNICAL FIELD

The disclosure relates generally to hospital carts and other healthcare delivery systems, and, more particularly, to a power system for a hospital cart.

BACKGROUND

Generally, power supplies for hospital carts, also referred to as medical carts, are uninterruptable power supplies that fall under two general categories: AC (alternating current) output or DC (direct current) output. The AC output uninterruptable power supplies provide a flexible configuration for the end-user because they offer 120 VAC outlets for use, similar to the typical 3-prong NEMA-style wall outlet. An example of an AC output uninterruptable power supply is the HC150 series power system provided by Tripp Lite, which may be paired with either a sealed lead acid (SLA) battery or lithium battery. The Tripp Lite AC output uninterruptable power supply has advantages such as fast recharge times, self-cooling (good heat dissipation), high power output and low operational noise. However, the AC systems are generally large and heavy, require AC-rated cables to power the medical cart components (e.g., AC-rated cables have double-insulation requirements for Mains voltage per industry standards, such as the International Electrotechnical Commission/Underwriters Laboratories (IEC/UL) 60601 technical standards for medical electrical equipment), and do not have wide-ranging input (i.e., they have specific input voltages, generally 120 VAC or 240 VAC).

The DC output uninterruptable power supplies are not flexible, in the sense that only very specific DC voltages and connectors can be used for the different equipment installed on the cart. However, DC output uninterruptable power supplies do provide increased efficiencies when running off the battery, which manifests in longer runtimes for the end user. An example of a DC output uninterruptable power supply is the medical-grade Series 301 Motive DC Controller provided by Hoffman Engineered Systems (HES), which are comparably smaller and lighter than their AC counterparts. The HES DC output uninterruptable power supply has advantages such as wide-range inputs, configurable outputs (e.g., DC/DC conversion to a different voltage with a converter or a DC/AC conversion with an inverter), and less wasted power due to conversions to different electrical outputs. However, the power cabling (e.g., power bus) in the cart must be rated for DC voltage per the above-mentioned industry standards, and the DC systems do not provide conversions to AC without an external DC/AC inverter.

While each has its advantages and disadvantages, the medical carts are designed and built around the power system. Thus, the medical cart is either a DC-based system or an AC-based system, thereby inheriting not only the advantages but also the disadvantages. The hardware for the medical cart is specific to either DC components or AC components. Although DC systems are somewhat configurable in being able to accommodate DC/DC converters, both AC and DC systems are limited in terms of configuring the power system and components of the medical cart. That is, the carts were, in part, designed around the power system, rather than the power system being designed around the cart, due to the "off-the-shelf" nature of uninterruptable power supplies from the power supply industry. This leads to less customization of medical carts for the end-user's purposes. The power system, and as a result the medical cart hardware components, are static, and not capable of being easily interchanged without modifying almost every aspect of the medical cart. While AC and DC systems each have their advantages, their respective disadvantages require the manufacturer (or the customer) to make tradeoffs when designing and building the medical cart.

Furthermore, based on the physical configuration of medical carts, the uninterruptable power supply, including the battery, is located in the base of the cart, near the floor, to help lower the cart's center of gravity. Any conversion modules (such as DC/AC inverters) are likewise provided in the base with the power supply, often as units external to the power supply. The end user's equipment (computer, monitor, printer, etc.) is located at the top of the cart with the work platform, close to the end user's upper body. Because of the engineering differences between the AC and DC power cables and connectors (they are not interchangeable), existing medical carts are set up with different stock keeping units (SKUs) for each power system configuration. Some medical carts are available with both AC and DC output power systems, but these configurations are inherently more expensive, and also require both sets of electrical cables and connectors to be routed from the base up to the work platform of the cart. As such, existing uninterruptable power supplies for medical carts prevent cart manufacturers from optimizing the medical carts for productivity, serviceability, and flexibility tailored for the customer.

Thus, there is a need to provide a hospital cart power system that is more flexible in terms of its configuration.

DETAILED DESCRIPTION

Disclosed herein is a power system for a hospital cart having a single uninterruptable power supply configuration within a base of the hospital cart that outputs DC power, with the DC power routed up a DC power bus in a support column to output power modules in the work platform which convert the DC power to a different state, such as AC power or DC power having a different voltage, in order to provide power to various components of the cart. Features of the power system may include, but are not limited to, interchangeability and replacement of the output power modules, and easier customization of the power system per the end-user's power requirements. Thus, the manufacturer may utilize the same power supply for all carts, changing only the output power modules per the end-user's requirements, thereby optimizing manufacturing, manufacturing cost and flexibility. This is possible because only small, inexpensive output power modules need to be designed and not the entire uninterruptable power supply in the base of the cart. For example, this architecture allows the manufacturer to build one configuration of cart all the way through the production process, except for the last step at which time the customer's selected output modules are installed. This architecture also allows the customer to easily change the output modules in the field, if the customer's needs change after the hospital cart has been received and fielded, including retrofitting existing cart systems. Although described primarily with respect to a hospital cart, the power system disclosed herein is further suitable for a variety of mobile equipment cart applications in medical environments including, but not limited to, hospitals, doctors' offices, in-home care, long-term care, ambulatory surgery centers, clinics, school health facilities, penitentiary health facilities, etc.

In one embodiment, the hospital carts are built around a single uninterruptable power supply configuration, located in the base of the cart, which outputs 24 VDC power. A 24 VDC power bus, such as power cables rated for direct current, then route power up the support column of the cart to the end user's work platform, where different modular output power modules can be integrated into the work platform depending upon the end user's output power desires. Potential output power configurations may include, but are not limited to: 24 VDC unregulated (20-30 VDC) at 150 W, 19.2 VDC regulated at 150 W and 120 VAC regulated at 150 W. The end user may select any one output power module or combination of output power modules, and the manufacturer or field service technician is able to add the appropriate modules to the cart with minimal effort.

Figure 1:
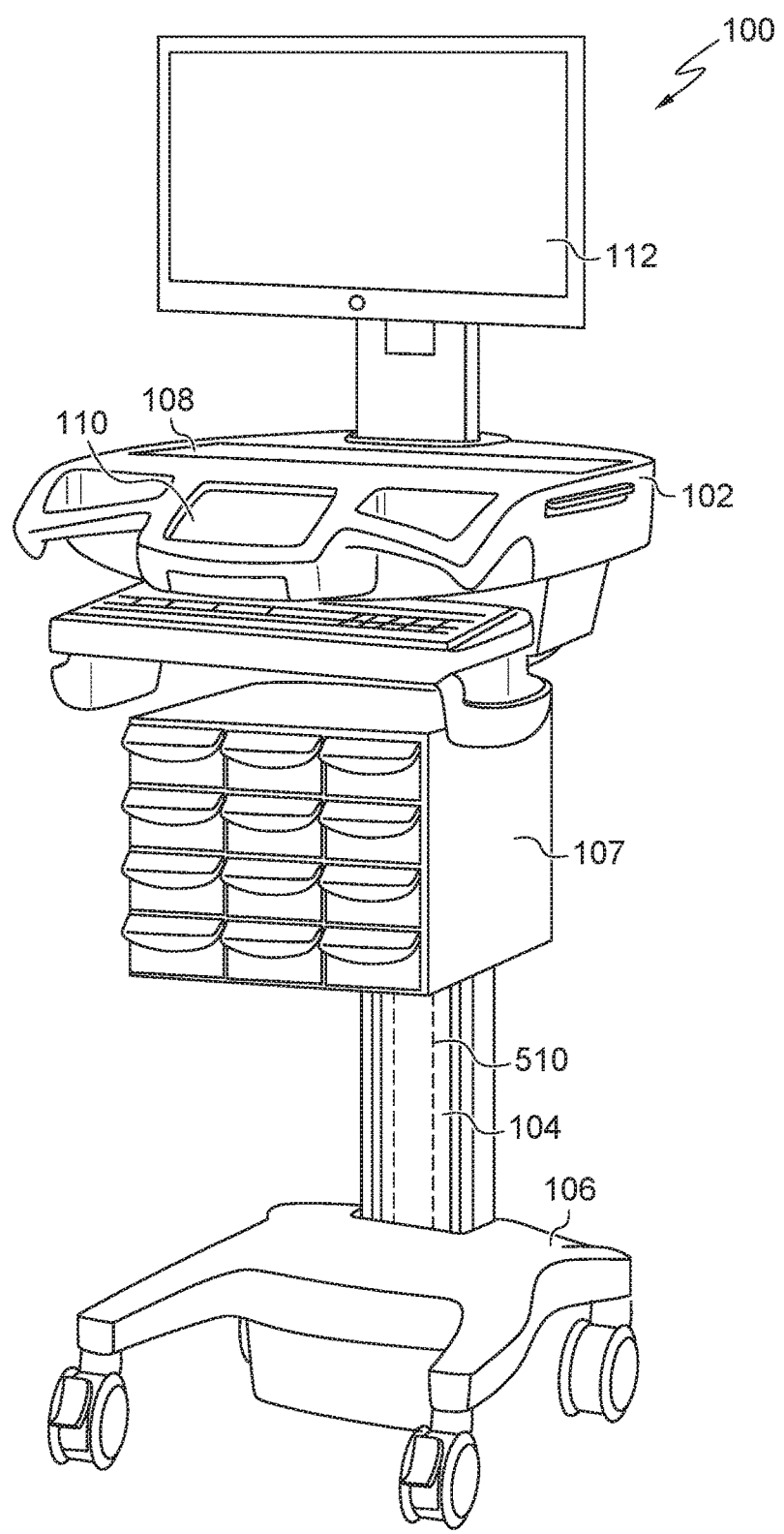
FIG. 1 is an exemplary perspective view of a medical cart in accordance with an embodiment.

FIG. 1 is an exemplary perspective view of a hospital cart 100. With respect to FIG. 1, the exemplary hospital cart 100, referred to hereafter as a medical cart 100, includes a work platform 102, a support 104 that supports and adjusts the height of the work platform 102, and a base 106 affixed to the bottom of the support 104. Optionally, the medical cart 100 includes one or more drawers 107, which may include manual or electric locks.

The work platform 102 of FIG. 1 houses an embedded computer, also referred to as a control system or hereinafter as a controller, having a computer-readable memory for storing instructions for cart operations and control cart functions, such as an embedded operating system kernel, for example, and a processor for executing those instructions/operating system. The work platform 102 further includes a work surface 108 and a display unit 110. The display unit 110 may be provided as a touch-sensitive display utilizing any of a number of display and touch screen technologies, including, but not limited to, cathode ray tube (CRT), liquid crystal display (LCD), light emitting diode (LED) LCD, organic light-emitting diode (OLED), projection, capacitive touch screens and resistive touch screens. The display unit 110 provides for control of the medical cart 100 via a display screen, which displays various controls as different display areas or display sections that a user can select by touching the display section corresponding to the desired commands in order to provide corresponding inputs to the controller for controlling the cart operations and cart functions. In particular, the display screen may display a dynamic, customizable GUI, examples of which are provided further below, which may be stored in the memory of the controller and executed by the processor as a separate application in the application layer above the embedded operating system kernel. The GUI displays relevant medical cart information to the end-user and enables the end-user to control system functions. System functions include, but are not limited to, power system and battery status, drawer access, electronic lift, a directional-locking caster function, keyboard/work-surface/ground lighting functions, service requests, notifications, and user preferences.

In one embodiment, the work platform 102 accommodates a user's computer, such as a laptop, thin client or zero client, which may be placed within an opening under the work surface 108, where the back of the work surface 108 includes a further opening to permit the display of the user's computer to extend out from the back of the work surface 108. In another embodiment, shown in FIG. 1, the medical cart 100 may accommodate a user's display monitor 112 attached to a monitor support affixed to the work platform 102, using a bracket and mount, with the user's computer operatively coupled to the display monitor 112 via a cable connection in the opening under the work surface 108 and extending through the monitor support or through the work platform 102 to the user's display monitor 112.

Additional features of the work platform 102 include external connections to the medical cart controller (e.g., USB ports), a variety of storage bins, a variety of work lights operatively coupled to the controller, pull-out shelves to extend the work surface 108 of the work platform 102, and handle grips. The work lights may be provided as LED lights, including, but not limited to, a keyboard light positioned above a keyboard platform, a work surface light position above the work surface 108 and one or more ground lights to illuminate the path in which the medical cart 100 is being moved. The handle grips may be used to move the medical cart 100 into position for the user, including adjustment of the height of the work platform 102, particularly if a mechanical (non-motorized) lift is provided. Under the handle grips, controls may be provided, including a steer-assist trigger to engage directional-locking casters to assist the user in moving the medical cart 100, and a height lever to engage adjustment of the height of the work platform 102 if a motorized lift is provided.

A power bus is provided within the support 104, running from power supply in the base 106 at the bottom or lower end of the support 104, where it is electrically coupled to the power supply therein, to the work platform 102 at top or upper end of the support 104, where the power bus is electrically coupled to the power output modules in the work platform 102. Generally speaking, the power bus is a DC power bus, such as one or more power cables rated for DC power. As mentioned above, in one embodiment the DC power bus is provided as power cables rated for direct current.

Figure 2:
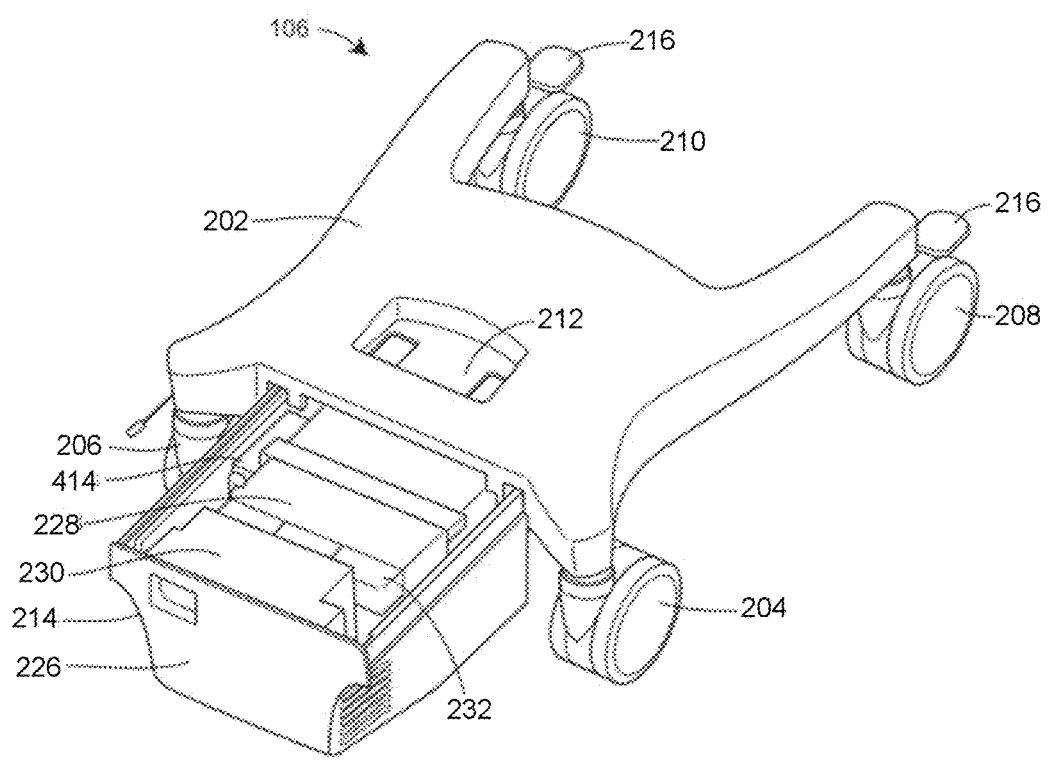
FIG. 2 is an exemplary perspective view of a base of the medical cart of FIG. 1 in accordance with an embodiment.

FIG. 2 depicts an embodiment of the base 106, which includes a main body 202 and multiple casters 202-210 affixed to the bottom of the main body. The main body 202 further allows for the support 104 to be affixed to the base 106, an example of which is shown as a depression 212 having the same shape and dimensions as the cross-section of the support 104, such that the lower end of the support 104 may be placed in the depression 212 and securely fastened to the base 106 using screws, bolts and nuts, or any other fastening system, as generally understood by those of ordinary skill in the art. As seen in FIG. 2, the depression 212 includes openings to a power supply 214 provided underneath the main body 202, thereby allowing connection to be made to the power bus in the support 104.

Each of the casters 204-210 may be swivel casters that can rotate in any direction on the main body 202, thereby allowing for movement of the medical cart 100 in any direction. Generally, one or more of the casters, such as the casters 208, 210 facing the back of the medical cart 100, may have a locking mechanism 216 to prevent the wheel of the caster from rotating, thereby preventing or resisting movement of the medical cart 100. A user may engage the locking mechanism 216 by pressing down on a tab to cause the locking mechanism 216 to engage the wheel, for example by friction, a protrusion engaging a notch, or other caster locking mechanisms as known by those of ordinary skill in the art. Lifting up the tab releases the locking mechanism. Optionally, one or more of the casters 204-210 may be provided as a directional-locking caster that locks the caster in place to limit the directional movement of the medical cart 100, for example, forwards and backwards, to assist the user in steering the medical cart 100.

The power supply 214 in the base 106 is provided as a single-platform uninterruptable power supply within a compartment 226 beneath the main body 202. The compartment 226 may be mounted to the main body 202 on rails affixed to the bottom of the main body 202, such that the compartment 226 may slide out like a drawer to allow for easy access to the power supply 214 and its components for service, retrofit, or exchange.

More particularly, the power supply 214 includes a rechargeable battery 228, and a battery charger/power supply 230 for charging the battery 228 and which serves as a common power source for the entire medical cart 100. The battery 228 may be provided as a lithium battery, a sealed lead acid (SLA) battery, a nickel cadmium battery (NiCd), nickel metal hydride battery (NiMH) or any other type of battery capable of powering the medical cart 100 components as understood by those of ordinary skill in the art. In one embodiment, the medical cart 100 may be provide with batteries of multiple types.

Different battery types (e.g., lithium, SLA, NiCd, NiMH, etc.) may require different methods of charging. Furthermore, the ability of the battery 228 to hold a charge and/or be recharged changes over time as the medical cart 100 is utilized and the battery 228 undergoes various cycles of charging and discharging. As such, the battery 228 includes a monitoring unit 232, which may be provided as an EEPROM or other passive memory devices, for storing the charge profile and parameters for the specific battery type used in the power supply 214. For example, the monitoring unit 232 may store various data such as the battery box serial number, model number, build date, current battery charge, last known fuel gauge value, battery fault data (e.g., over temp and over current), etc., as well as the particular charging parameters associated with a given battery 228. Examples of charge parameters for a battery include, but are not limited to, float, bulk, overcharge, cutoff and recovery voltage and current ranges specified by the battery manufacturer for charging, battery discharge cycle count, rated number of discharge cycles (useful service life of the battery), percent reduction in capacity after the rated number of discharge cycles, rated ampere-hour (AHr) capacity, aged capacity, pro-rated discharge current and partial discharge cycle count.

The monitoring unit 232 may be coupled to the battery charger 230 via a communications bus as part of the charging operation of the battery 228, and to provide the information about the battery 228. For example, during system startup of the medical cart 100, the monitoring unit 232 may upload the battery information to the charger 230. The monitoring unit 232 may further be communicatively coupled to the controller in the work platform 102 to provide information about the battery 228, such as the current battery charge, last known fuel gauge value, battery fault data (e.g., over temp and over current), cycle count, and battery charge/discharge parameters. In one embodiment, the monitoring unit 232 is provided with a microcontroller, such that the battery 228 is a smart device that may receive software or firmware updates. Furthermore, the monitoring unit 232 may be provided as a printed circuit board, integrated circuits, application specific integrated circuits (ASICs), controllers, programmable logic devices, etc. as understood by those of ordinary skill in the art.

The charger 230 may read the battery data from the monitoring unit 232 upon system power-up for purposes of identifying appropriate charge parameters and relevant system data, and write data to the monitoring unit as appropriate during system operation. One function of the charger 230 is to monitor the charge in the battery, both as it discharges and while it is charging. This function is referred to as the "fuel gauge" which may be represented on the display unit 110 via the user interface. The fuel gauge may range from 0-100%, having a resolution in single digits, and may further include a time-to-charge display showing the estimated or calculated time until the battery is fully charged and a time-to-discharge display showing the estimated or calculated time until the battery is fully discharged (or discharged beyond its cutoff voltage) once AC power has been disconnected. Data from the monitoring unit 232 may be taken into consideration when determining battery status, charging the battery and fuel gauge.

For example, rechargeable batteries have a useful life which is quantified as the number of accumulated discharge cycles which the battery can deliver. After the specified number of discharge cycles, the delivered AHr capacity of the battery is reduced by a specified amount (e.g., the AHr capacity in an SLA battery is reduced by 40% after 300 discharge cycles). From a practical standpoint this is considered the end of the useful service life of the battery, as the battery capacity will start to dramatically degrade with further use after the specified number of discharge cycles. The reduced AHr capacity of the battery 228 due to the aging effects caused by accumulated discharge cycles (Aged Capacity) as stored in the monitoring unit 232 may be taken into account by the charger 230 when determining the fuel gauge value and charge time remaining in a battery 228.

The number of discharge cycles rated for the battery 228 as stored in the monitoring unit 232, specifies the useful service life of the battery (as specified by the battery manufacturer). The rated number of discharge cycles, as well as the percentage reduction in capacity after the rated number of discharge cycles as also stored in the monitoring unit 232, may be used to quantify the aging effects of the battery 228. The aged capacity of the battery 228 as stored in the monitoring unit 232 may then be calculated by the charger 230 as:

$$AgedCapacity = Rated\ AHr\ Capacity[100-(\%\ Reduction*DischargeCycles/RatedCycles)]$$

The rated AHr capacity for a battery 228 as stored in the monitoring unit 232 is typically specified by the battery manufacturer for a low rate of current discharge where the charge of the battery is extracted over a 20 hour period. An increase in discharge current beyond the low rate of discharge current results in an apparent reduction in AHr capacity of the battery 228. This has practical implications for calculating the fuel gauge value, remaining battery run time, etc.

The fuel gauge value during discharge is decremented by the pro-rated discharge current, I_Discharge, for each time interval that the charger 230 measures and adjusts the fuel gauge level.

The battery discharge cycle count as stored in the monitoring unit 232 counts the number of times that the battery 228 has been discharged. The discharge cycle is a cumulative, pro-rated AHr discharge equal to the AHr rating of the battery 228. The cumulative discharge may or may not be interrupted by one or more charge cycles. The accumulation of the pro-rated AHr rating of the battery 228 increments the discharge cycle count by one. The charger 230 monitors and tabulates the number of complete battery discharge cycles, and periodically transmits the count to the medical cart controller. The discharge cycle count may implicitly include the measured current pro-rating as it accumulates AHr discharge. The discharge cycle count is used to estimate the expected end of life for the battery, and is written to the monitoring unit 232 so that a battery 228 separated from the power supply 214 retains the cycle count data for service, returns, repairs, etc.

The partial discharge cycle count as stored in the monitoring unit 232 may be stored prior to the charger 230 disconnecting the battery 228 from the power system or shutting down the battery due to the battery exceeding a temperature threshold. The partial discharge cycle count may then be retrieved for a recovery from an over-temperature shutdown and/or a power-on reset. This may be implemented as a rolling discharge cycle count with an increment of one tenth of a cycle.

In addition to the above-discussed battery data stored in the monitoring unit 232, the monitoring unit 232 may include safety devices, such as fault detection devices for detecting over temperature and over current. For example, the monitoring unit 232 may include a thermistor for sensing the battery temperature. The thermistor leads may be routed back to the charger 230, and the charger 230 may bias the thermistor and read the temperature, such that the charger 230 is able to monitor the temperature of the battery 228. The charger may then adjust the charge voltage setpoints to compensate for temperature changes in the battery 228. Also, the charger 230 may take appropriate safety measures such as reducing the charge current and/or disconnecting the battery 228 in the event of a sensed over-temperature condition, in which case the charger 230 may signal a fault condition to the medical cart controller.

In addition to the charger 230 monitoring the battery temperature, the monitoring unit 232 may include a thermal disconnect device, which is a hardware shutdown function that overrides control from the charger 230 and/or the medical cart controller in the event of a severe over-temperature fault in the battery 228. This safety device may be provided as a bi-metallic switch having a metal plate in close thermal proximity to the battery 228 in order to measure severe over-temperatures (e.g., 60-70° C.). As is understood by those of ordinary skill in the art, a bi-metallic switch comprises two pieces or plates of metal, with one piece/plate of metal that bends faster than the other piece/plate of metal when the temperature rises, such that if the temperature reaches a certain threshold, the bending metal piece/plate bends enough to open the switch. The thermal disconnect device self-resets once the battery temperature has reduced to a safe level. In this manner, system shutdown in the event of an abnormally high temperature condition in the battery 228 will not solely be dependent upon the system firmware, charger 230 and/or associated temperature monitoring devices.

Figure 3:
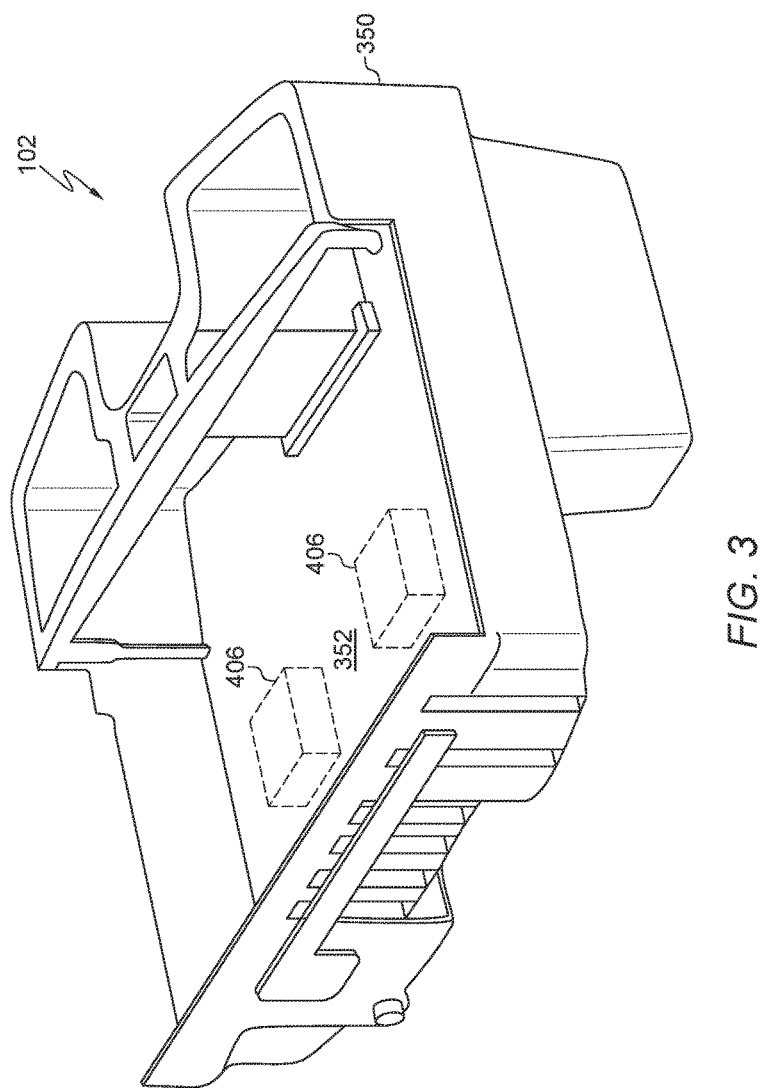
FIG. 3 is an exemplary perspective view of a work platform of the medical cart of FIG. 1 in accordance with an embodiment.

FIG. 3 depicts an embodiment of the work platform 102, and, more particularly, the sub-assembly of a technology box 350 which houses the controller, the end-user's computer and the output power modules. As seen in FIG. 3, the work platform 102 includes a deck area or surface 352. The work surface 108 may be removed or otherwise opened to reveal the deck area 352, where the end user may place the end user's computer. Beneath the deck area 352, the work platform 102 houses the output power modules, such as an AC inverter and/or DC/DC converters.

The controller 402 embedded within the medical cart may be provided as one or more memories, such as a hard disk, solid state hard drive, programmable ROM, RAM or other memory device, and further provided as one or more processors, such as central processing units (CPUs) or other computing devices that support an embedded operating system kernel, such as, for example, the Microsoft Windows™ Embedded CE 6.0 R3, Win7, Linux, Android, Ubuntu, etc. operating system kernels. The controller 402 further supports multi-threaded cart software application, a separate cart diagnostics software application, and a host of hardware interfaces.

Figure 5:
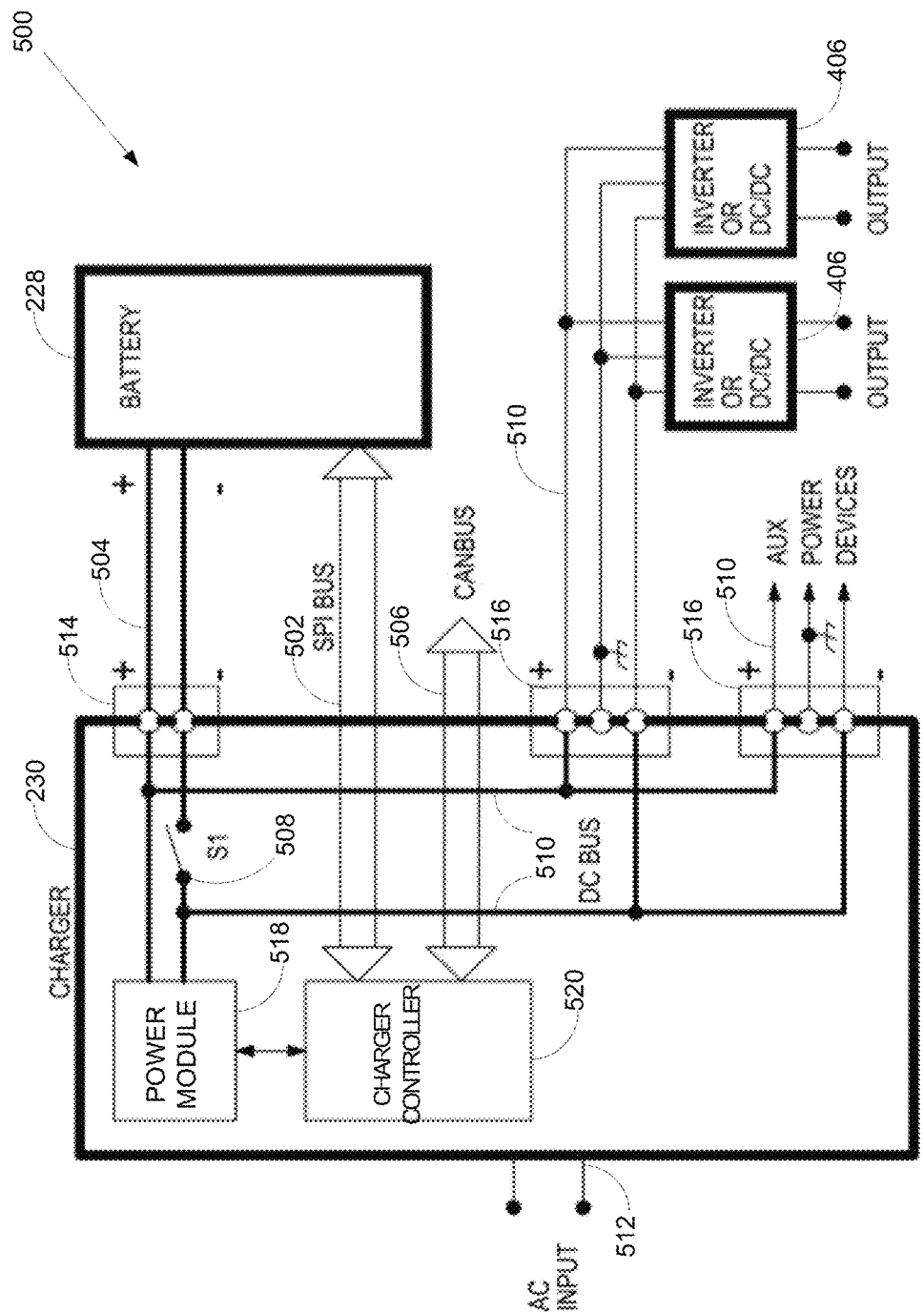
FIG. 5 is an exemplary block diagram of a power system of the medical cart of FIG. 1 in accordance with an embodiment.

FIG. 5 is an example of the power system of the medical cart 100 shown in a block diagram. Referring to FIG. 5, the power system 500 includes the charger 230, battery 228 and one or more modular output power modules 406. The charger 230 communicates with the battery 228, and specifically the monitoring unit 232, via a dedicated communications bus 502, such as a Serial Peripheral Interface (SPI) bus. The charger 230 is further electrically coupled to the battery 228 via a dedicated DC power bus 504 to charge the battery 228, and communicatively coupled to the controller 402 via a communications bus 506, which may be provided as a controller area network (CAN) bus, to communicate a complete set of power system data and operating parameters to the controller 402. As used above and herein, "electrically coupled" refers to the transfer or supply electricity (i.e., electrical power) from one component to power another component, whereas "communicatively coupled" refers to the communication of data from one component to another component. Those of ordinary skill in the art will understand that in some cases the physical connection between two components may both supply electricity to power a component and communicate data to that component (e.g., power line communications, power over Ethernet, etc.), but that transferring or supplying electricity to power a component (i.e., electrically coupled) is different than communicating data to or from the component (i.e., communicatively coupled), even where the data is communicated electrically.

The DC power bus 504 includes a switch 508 which electrically couples and uncouples the battery 228 to and from the power bus provided within the support 104, shown in FIG. 5 as a DC power bus 510 electrically coupled to the output power modules 406 and auxiliary DC power loads, such as a motorized lift, lighting, other DC motors, etc. Thus, when the switch 508 is closed, the battery 228 is electrically coupled to the DC power bus 510, and provides power to the output power modules 406 as well as auxiliary DC power loads. Although depicted as a mechanical switch, those of ordinary skill in the art will readily understand that the switch may be provided using electronic circuitry, including, but not limited to, suitably-rated power semiconductor devices and power ICs (integrated circuit).

When AC power, such as AC utility power or AC mains (e.g., 90 to 264 VAC, 47 to 63 Hz, single phase), is applied to the charger 230 via an AC input 512, the charger 230 supplies power to charge the battery 228 via a DC output 514 and the dedicated DC power bus 504, and also powers the output power modules 406 and auxiliary power loads via DC outputs 516 electrically coupled to the DC power bus 510. A power module 518 in the charger 230 converts the AC input power to the DC power necessary to charge the battery 228, as well as power the output power modules 406 and auxiliary devices. Both the voltage and current are controlled by a charger controller 520, which is communicatively coupled to the power module 518.

The charger controller 520 is further communicatively coupled to the battery 228, and specifically the monitoring unit 232, via the dedicated communications bus 502. For example, after a power-on reset of the charger controller 520, the charger controller 520 enters a boot-up mode and attempts to communicate with the battery 228, and specifically with the monitoring unit 232, over the SPI bus 502 and check for the presence of a battery voltage. If the charger controller 520 cannot establish a communication link with the battery 228, and detect a battery voltage above a minimum threshold (e.g., 10 VDC), the charger 230 may disconnect the battery 228 and enter a "No Battery Mode". In this mode of operation, the battery 228 may remain disconnected and the charger output (DC power bus 510) may be set to a constant operational voltage (e.g., 24.0 VDC) using the AC power source. Since there is no battery 228 connected to the system in this mode, there is no backup power and the DC power bus 510 will lose power if the AC power source is removed. The system may enter this mode either when there is no battery 228 present, or when the charger 230 has determined that the battery 228 is not operating properly.

As long as the AC power is applied to the charger 230, the dedicated DC power bus 504 may supply power to charge the battery 228 with the switch 508 closed, and the DC power bus 510 may provide power to any installed output power modules 406 and other auxiliary power loads. When AC power is not being applied to the charger 230, and the switch 508 is closed, the battery 228 is effectively connected to the DC power bus 510. This allows the battery 228 to power the installed output power modules 406 and auxiliary loads when AC power is not present. In the event a fault is detected with the battery 228, or no battery is present, the switch 508 may be opened.

Figure 4:
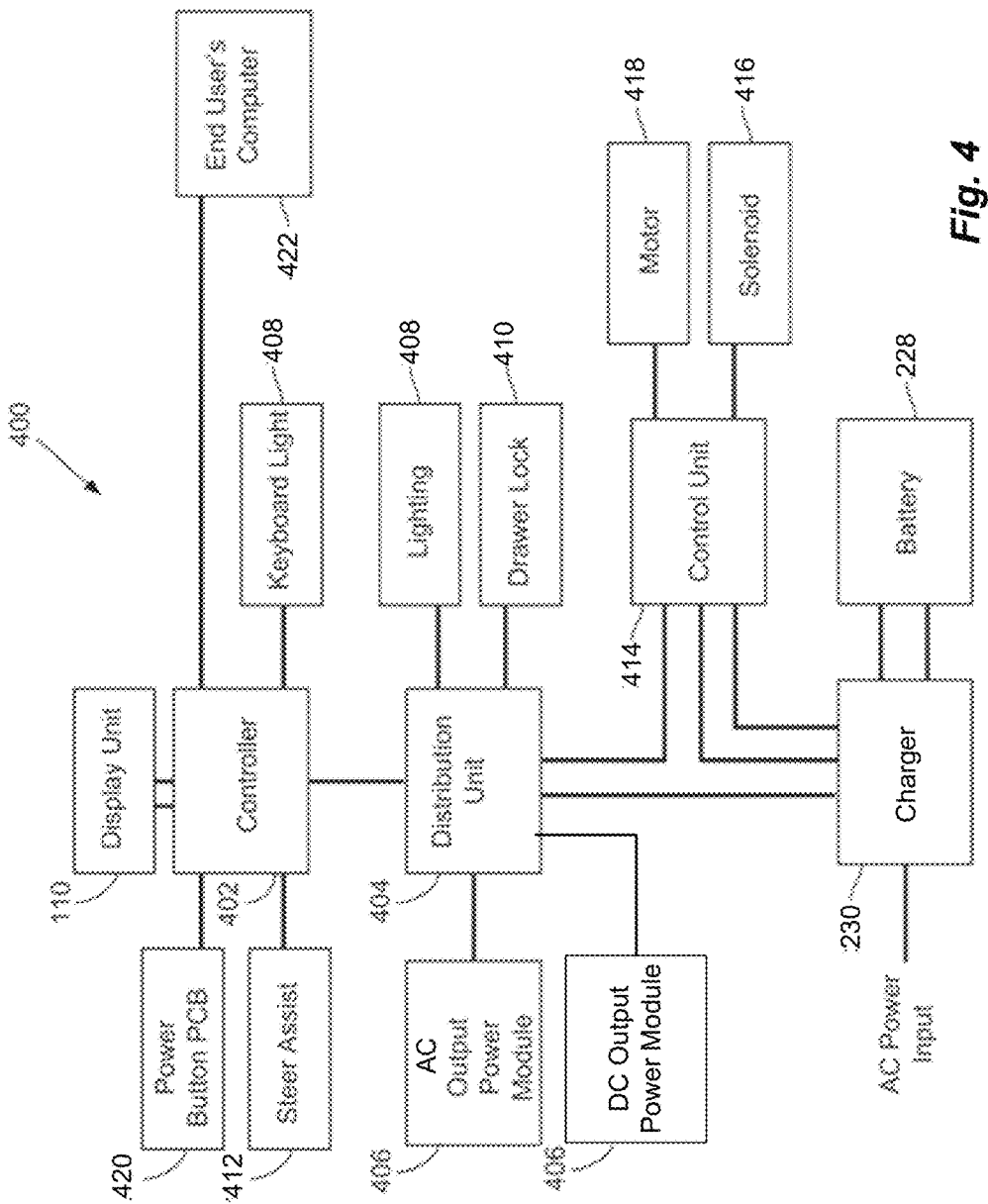
FIG. 4 is an exemplary schematic diagram of various components parts of the medical cart of FIG. 1 in accordance with an embodiment.

FIG. 4 is an exemplary schematic diagram of various electrical component parts 400 of the medical cart 100. In particular, the medical cart controller 402 is operatively and communicatively coupled to a power and communication distribution unit 404, which, in turn, is connected to output power modules 406, such as an AC inverter and a DC/DC converter output power modules, and the battery charger 230, which, in turn, is connected to the battery 228. These form the core components of the medical cart's electrical power and communications system. Additional components, some of which have been described above, may include work lights 408, drawer locks 410, a steer assist trigger 412, a control unit 414 and associated solenoid or servomotor 416 for directional-locking casters and/or motor 418 for a motorized lift, a power button 420 to power up the medical cart 100, and the end user's computer 422, each of which are operatively and communicatively coupled to the controller 402 either directly or via the distribution unit 404. The distribution unit 404 may be provided as a printed circuit board, integrated circuits, application specific integrated circuits (ASICs), controllers, programmable logic devices, etc. as understood by those of ordinary skill in the art.

Figure 6:
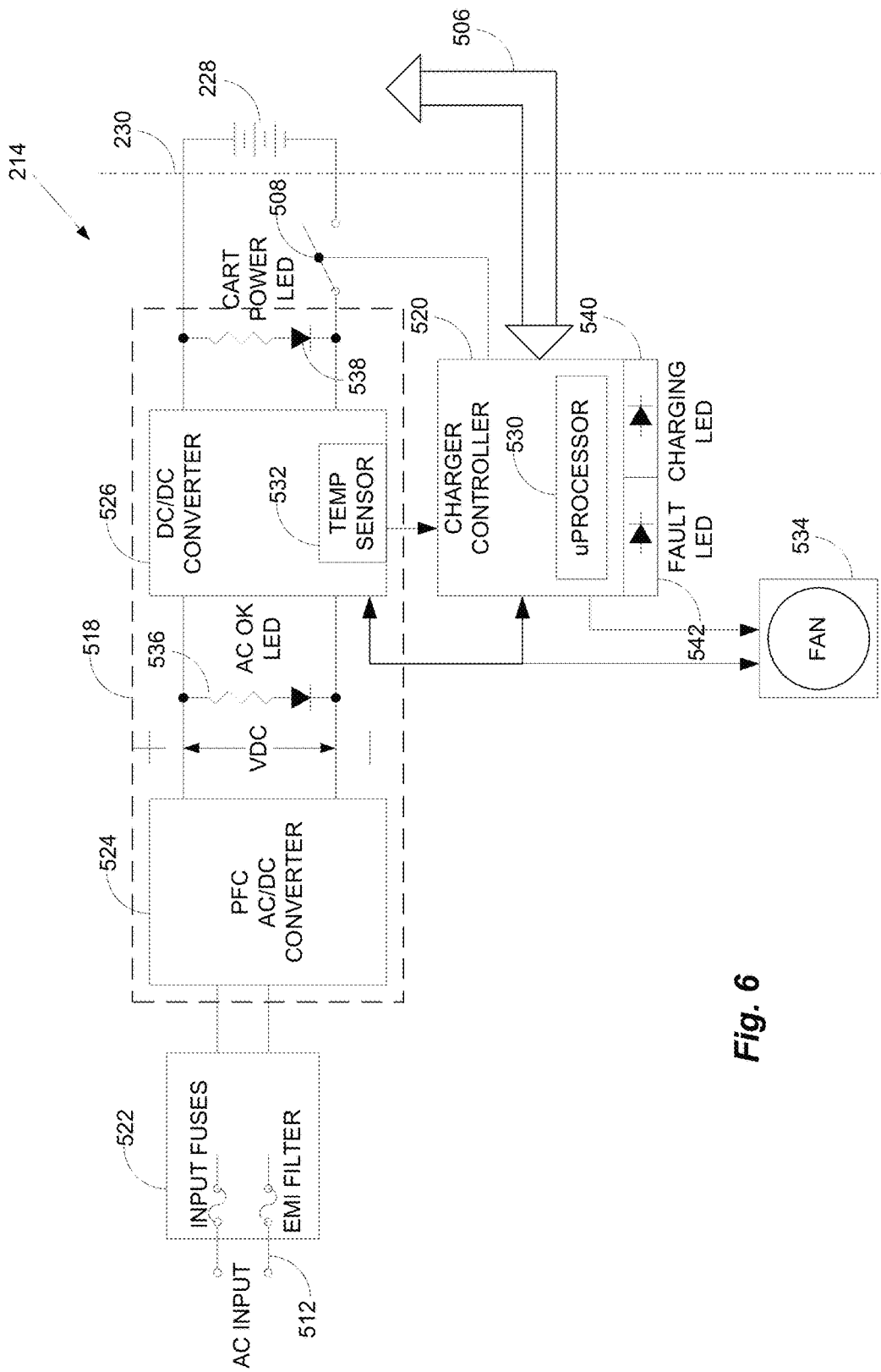
FIG. 6 is an exemplary block diagram of a power supply of the power system of FIG. 5 in accordance with an embodiment.

FIG. 6 is an example of the power supply 214 of the power system 500 shown in a more detailed block diagram format. Generally speaking, the power supply 214 includes the charger 230, the battery 228. The charger 230 is a "smart" charger in that the charger 230 has a microprocessor which enables the charger 230 to identify the battery type (e.g., lead acid, lithium ion, NiCd, NiMH, etc.) and battery capacity using, for example, information from the monitoring unit 232, in order to provide the optimum charge profile for charging the battery, examples of which were provided above. This helps ensure optimal battery cycle life, fast recharge times and safe operation for different battery chemistries and battery capacities. Additionally, the charger 230 provides the controller 402, and, in turn, the user, with accurate information for recharge time, run time under varying load conditions, battery status, temperature, cycle count and related power system information.

Referring to FIG. 6, charger 230 may be provided with the AC input 512, which may be a universal AC input, such as an International Electrotechnical Commission (IEC) plug, that can receive a current from a standard 120 VAC or 240 VAC outlet. The plug may be exposed through an opening, shown in the front of the compartment 226 in FIG. 2, to permit connection to a power cable to electrically couple the AC input 512 of the charger 230 to the AC power supply. The AC input 512 may be associated with a power entry module 522 having an input cutoff fuse and electromagnetic interference filter prior to inputting the AC power to the power module 518. In particular, the input may be fuse-protected in both the line and neutral connections. For example, the fuse may be set such that the fuse is tripped if a inrush surge from a cold start of the system exceeds 40 amps peak, for 3 cycles maximum, of the mains frequency under any conditions for any value of the mains voltage within the specified range.

The power module 518 of the charger 230 includes a power factor correction (PFC) AC/DC converter module 524, and a DC/DC converter module 526. The PFC module 524 operates off the AC input voltage to create a "universal front end" which accepts the AC input power. The PFC module 524 powers the DC/DC converter 526 which produces DC power (e.g., in the range of 20 VDC to 30 VDC) to charge the battery 228, as well as power the output power modules 406 and auxiliary power devices. The output voltage and current of the DC/DC converter 526 are controlled by the charger controller 520, which includes a microprocessor 530.

The charger controller 520 also monitors the temperature of the charger 230 via a temperature sensor 532. If the temperature exceeds a threshold, which may be indicative of decreased airflow due to clogged vents, fan malfunction, overcurrent situation, etc., the charger controller 520 may cause the DC/DC converter 526 to cease charging the battery 228 and/or cease powering the output power modules 406 and auxiliary power loads. In the case of a temperature fault, the charger controller 520 may communicate the fault and associated information to the cart controller 402.

The charger controller 520 may further activate and control the speed of a charger cooling fan 534 (e.g., half speed, full speed, off) based on the temperature of the charger 230. In particular, based on the temperature from the temperature sensor 532, the charger controller 520 may activate the fan 534 to cool the charger 230 in response to a particular temperature, increase the speed in response to an increase in temperature, decrease the speed in response to a decrease in temperature and deactivate the fan if the temperature falls below a particular temperature. An example of the control of the fan and current based on temperature is provided in Table 1 below:

TABLE 1

| State | Charger Temperature | Current | Fan Speed | Condition/Action |
|---|---|---|---|---|
| 1 | 0° C. | 100% | 0% | Normal Operation |
| 2 | 35° C. | 100% | 50% | Back to State 1 at 30° C. |
| 3 | 55° C. | 100% | 100% | Back to State 2 at 50° C. |
| 4 | 65° C. | 50% | 100% | Back to State 3 at 60° C. |
| 5 | 75° C. | 0% | 0% | Unit Shutdown. Back to State 1 at 35° C. |

From the example above, if the charger 230 is less than 35° C. (State 1), the charger 230 is considered to be running normally, such that the fan 534 may be turned off and the current provided at 100%. Between the temperatures of 35° C. and 55° C. (State 2), the charger controller 520 may control the fan 534 to run at half speed, and change to State 1 when the temperature lowers to 30° C. Between the temperatures of 55° C. and 65° C. (State 3), the charger controller 520 may control the fan 534 to run at full speed, and change to State 2 when the temperature lowers to 50° C. Between the temperatures of 65° C. and 75° C. (State 4), the charger controller 520 may maintain the fan speed at 100%, but reduce the current to 50% as part of cooling the charger 230, changing to State 3 when the temperature lowers to 60° C. At 75° C. or above, the charger controller 520 may shutdown the charger 230 entirely, and change to State 1 only once the charger 230 has cooled to 35° C. As seen from the above example, when the temperature of the charger 230 cools, the charger controller 520 may be programmed to 5° C. of hysteresis before the fan switches to a lower speed or off. The varying speeds of the fan 534 reduces the audible noise and prolongs the life of the fan 534.

The charger controller 520 may include a variety of status lights, provided as light emitting diodes (LEDs) or the like, which are primarily intended for service use, but may be viewable from the outside of the compartment 226. Examples of status lights include an AC input status light 536, a cart power status light 538, a charging status light 540 and a fault status light 542. The charger controller 230 may directly control the charging status light 540 and fault status light 542, whereas the AC input status light 536 and cart power status light 538 are powered and controlled via the power entry module 522 and power module 518, respectively.

When the AC input status light 536 is lit, it indicates the presence of AC input power, and that the power entry module 522 and AC/DC module 524 of the charger 230 are operational. If an input fuse in the power entry module is blown and/or the AC/DC module 524 is inoperable, the AC input status light 536 is off. The AC input status light 536 is dependent on the operation of the power entry module 522 and the AC/DC module 524, irrespective of the presence of the battery 228 and operability of the charger controller 520.

The cart power status light 538 is lit if the DC power bus 504 is above a minimum voltage threshold (e.g., 20 VDC) necessary to power the output power modules 406 and auxiliary power loads, regardless of whether the DC voltage is a result of the AC power being applied to the charger input 518 to produce the DC output voltage or if the battery 228 is supplying the DC output. This LED may be lit even if there is no battery 228 present.

The charging status light 540 is controlled by the charger controller 520, and is lit when the charger is in a valid charge state. The charging status light will be unlit if the battery 228 is not present, or if the charger controller 520 has disconnected the battery 228, for example, via the switch 508, due to a fault condition. The fault status light 542 is a summary fault indicator and is likewise controlled by the charger controller 520 to indicate a fault detected with the charger 230.

The temperature of the battery 228 is also monitored by the charger controller 520, for example via the temperature sensor or temperature safety device in the monitoring unit 232. For example, the charger output may be varied based upon a temperature compensation scheme to modify charger output voltage and/or output current via the DC/DC converter 526 based upon battery temperature. If the battery 228 exceeds a safe operational temperature (e.g., 75° C.), the charger controller 520 controls the charger output voltage and current via the DC/DC controller 526 to zero, and issues a command to the switch 508 to disconnect the battery 228. Once the temperature of the battery 228 falls to a safe or normal operating temperature (e.g., 35° C.), the charger controller 520 will attempt to reconnect the battery 228 and resume operation.

As seen from the description of FIGS. 5 and 6 above, the current from the charger 230 splits to power the output power modules 406, the auxiliary loads and to charge the battery 228. If the combined load demands exceed the power rating of the charger 230, the charger controller 520 allows the output power modules 406 to take priority over power to recharge the battery 228 so as to guarantee the operation of the work platform 102. Under these conditions, the battery 228 recharge time will increase since the full recharge current is not available.

Figure 7:
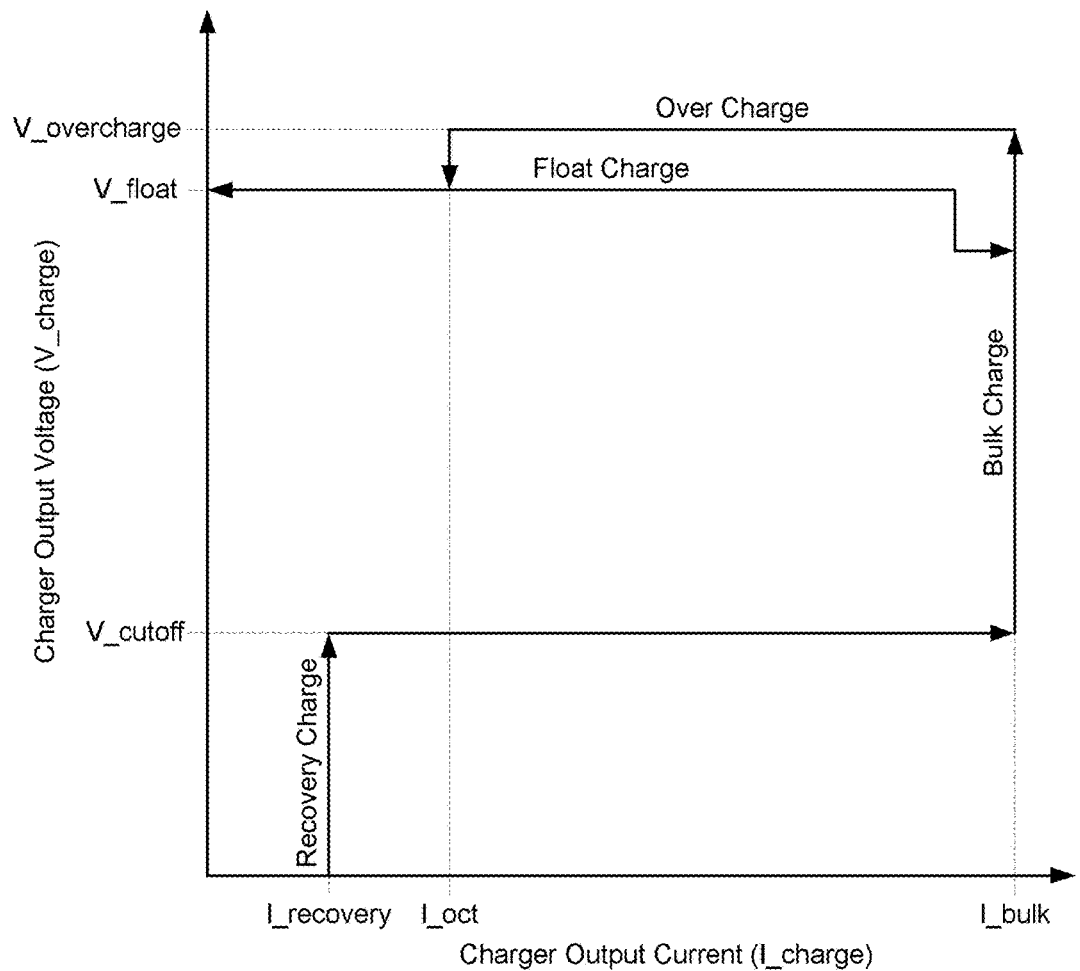
FIG. 7 is an exemplary graph of the charging states of a charging module in accordance with an embodiment.
Figure 8:
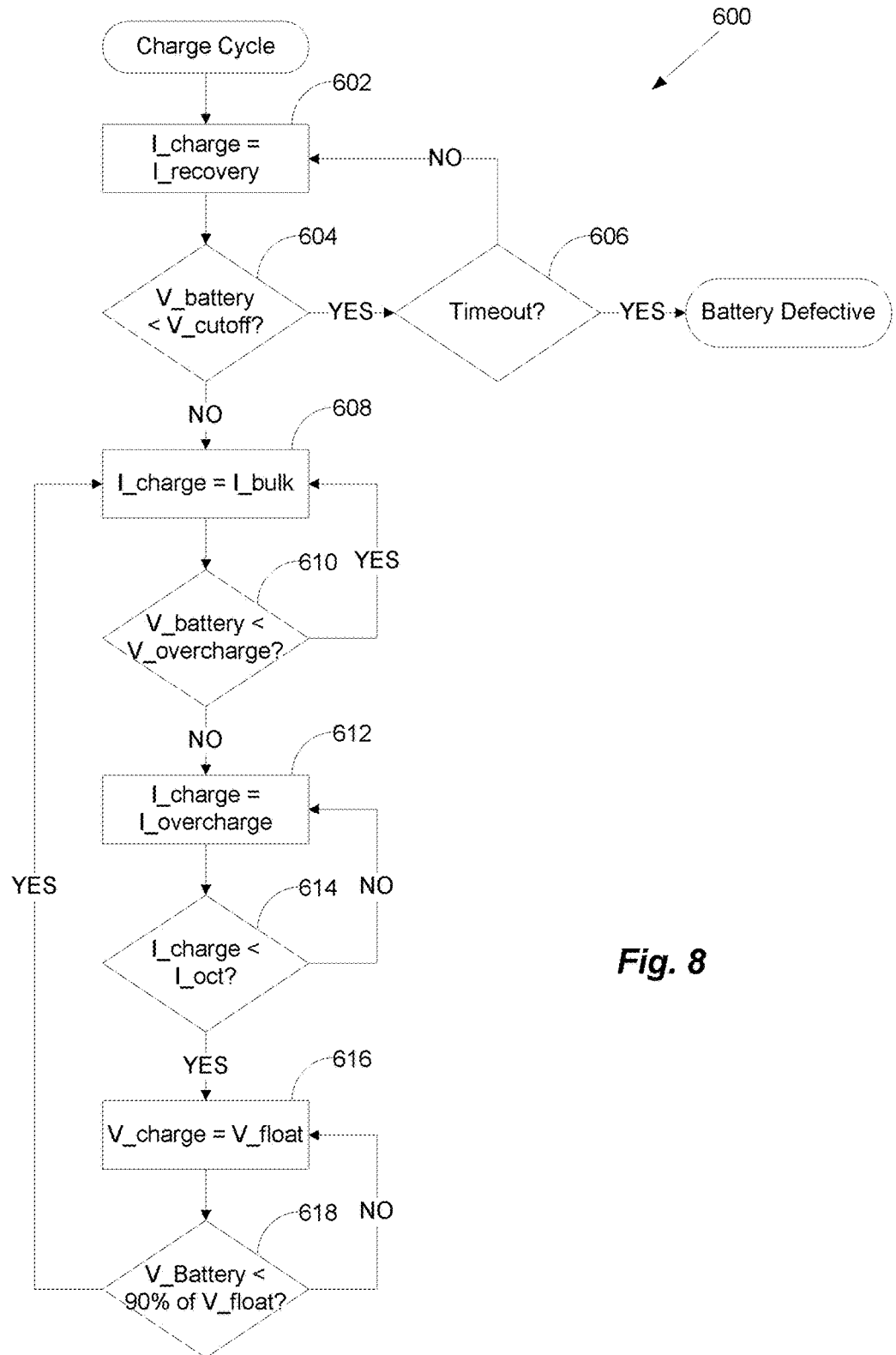
FIG. 8 is a flowchart of the operation of a charging module transitioning the charging states of FIG. 7 in accordance with an embodiment.

As shown in FIGS. 7 and 8, the charger 230 utilizes a multiple-state charging function 600 which charges, maintains and controls the battery 228. In this example, the charger 230 employs four states, each corresponding to a different charging voltage or current: Recovery Mode; Bulk Charge; Over Charge; and Float Charge. The charging state is dependent upon various defined voltage points and current points, which mark the transition from one charging state to another, as monitored by the charger controller 520 which, in turn, controls the DC/DC converter 526 to adjust the charging current and voltage for the battery 228. In this example, the voltage and current setpoints include, but are not limited to: battery cutoff voltage (V_cutoff); battery overcharge voltage (V_overcharge); floating charge voltage (V_float); over-discharged charge current (I_recovery); maximum charge current (I_bulk); and overcharge threshold current (I_oct). Examples of these setpoints are provided in Table 2 below:

|  | Valence | SLA | Units |
|---|---|---|---|
| V_cutoff | 22 | 21.4 | V |
| V_recovery | 22 |  | V |
| I_recovery | 5 | 0.2 | A |
| T_recovery | 1 |  | Hrs |
| I_bulk | 10 | 4 | A |
| V_overcharge | 29.2 | 28.8 | V |

|  | Valence | SLA | Units |
| --- | --- | --- | --- |
| I_overcharge | 0.5 | 1.2 | A |
| V_float1 | 29.2 | 27.3 | V |
| V_float2 | 27.6 | 27.3 | V |
| T_overcharge | 1 |  | Hrs |
| T_float1 | 3 |  | Hrs |

Once the system is running, the charger controller 520 accumulates the net ampere-hours (AHr) of charge in the battery 228 based on any charge being applied to the battery 228 and based on any discharge from the battery 228 (AHr in minus AHr out). Reaching the various states during a charge or discharge flags the fuel gauge to reset to the proper values regardless of the prior AHr value. For example, at the end of the Float Charge state, the battery 228 should be at 100% capacity as reflected by the fuel gauge. In another example, if the battery 228 has discharged to a level in which the battery 228 was disconnected (e.g., the battery capacity has diminished to 0%) during a discharge cycle, the fuel gauge should be set to reflect 0 AHr capacity.

Further, any time the system loses the battery fuel gauge value, for example, due to accumulated error over a number of charge/discharge cycles, fault or unrecoverable error, the fuel gauge value may be estimated based on the measured battery voltage during the charge state. For example, if the battery voltage is at or near V_cutoff, the fuel gauge may be set to zero. If the battery is at the float voltage, V_float, the fuel gauge may be set to 95%. Voltages in between V_cutoff and V_Float may be linearly interpolated to calculate the available battery capacity or fuel gauge value.

Upon the application or re-application of AC power or by the assertion of a restart signal from the user interface, a signal may be transmitted to the charger controller 520, for example via the AC/DC module 524, indicating the presence of AC power to initiate the charge cycle. Referring to FIG. 8, the charger 230 may begin in the Recovery Mode state at block 602, for example, after a power-on reset of the charger 520 controller. A power-on reset may be experienced, for example, if the system disconnects the battery 228 due to a low battery condition (e.g., over-discharge), and the system is restarted by applying AC power to the charger 230 (e.g., by plugging in the AC power cord), at which point the charger controller 520 experiences a power-on reset. On the other hand, if the system did not experience a power-on reset (e.g., the battery was not disconnected), the charger controller 520 may enter the Bulk Charge state, described further below.

During the Recovery Mode state, the charging current for the battery, I_charge, is first set to the over-discharge charge current, I_recovery. The over-discharge charge current, I_recovery, is the charging current delivered by the charger 230 to the battery 228 when the battery voltage is less than the battery cutoff voltage, V_cutoff. In other words, if the battery has been over-discharged, such that its voltage level is below a threshold, V_cutoff, the charger 230 will charge the battery at a lower current, I_recovery, until the battery voltage reaches the cutoff voltage, V_cutoff. During the Recovery Mode state, the battery 228 receives this small charge current, I_recovery, in order to try to bring the battery 228 back to a specified operating range where the battery 228 is healthy enough to accept a full charging current (e.g., I_bulk).

The charger controller 520 may continually or periodically read the battery voltage at block 604, for example, via data from the monitoring unit 232, to determine if the battery voltage has reached V_cutoff. In order to avoid continuously trying to apply a small charge to a defective battery, a timer may be set to limit the maximum time spent in the Recovery Mode state (e.g., 1 hour). If the battery voltage has not reached the cutoff voltage, the charger controller 520 may determine whether the maximum time has been reached at block 606. If so, then the charger controller 520 may conclude that the battery 228 is defective, terminate the charge cycle, signal an error for the user to get the system serviced (e.g., via a message to a user interface on the display unit 110), and shut the charger 230 down.

During the Recovery Mode state (i.e., before timeout), the charger controller 520, or the cart controller 402, may set and display the charge time remaining on the user interface to indicate an indeterminate battery status. Any time the charger 230 is in the Recovery Mode state, the battery state of charge is assumed to be zero AHr, as reflected by the fuel gauge. Once the battery voltage has exceeded V_cutoff, as determined at block 604, the charger 230 transitions from the Recovery Mode state to the Bulk Charge state, though the fuel gauge is still zero AHr. The reasoning is that, as noted above, the Recovery Mode state is utilized when the battery 228 is over-discharged below V_cutoff, and I_recovery provides the battery 228 with a small charge current to bring it back to a healthy operating range to accept a full charging current, I_bulk. Therefore at the end of Recovery Mode, the battery is still considered to be at a zero state of charge, but ready to accept the maximum charge current, I_bulk.

At block 608, having charged the battery 228 to V_cutoff, or if the battery 228 has not been over-discharged below V_cutoff in the first place, the charger 230 enters the Bulk Charge state where the charger controller 520 sets the charging current, I_charge, from the DC/DC converter 526 to the maximum allowable charge current, I_bulk. The Bulk Charge state is the part of the charge cycle during which most of the charge is delivered to the battery 228. During the Bulk Charge state the charger controller 520, or the cart controller 402, may calculate and display the charge time remaining on the user interface to indicate the remaining charge time. The remaining charge time may be calculated as:

Charge Time Remaining(hours)=[Battery Rating (AHr)−Fuel Gauge(AHr)]/[Charge Current (amps)]

It is noted that the remaining charge time may be dependent upon the charge being drawn from the AC power source, namely the loads from the output power modules 406 and/or the auxiliary DC power loads. For example, the system may be in the beginning of the Bulk Charge state with full power being drawn from an inverter, allowing a maximum charge current of 3 amps. For a 20 AHr battery, the charge time would be around 7 hours. On the other hand, nearing the end of the Bulk Charge state, the charge time remaining may be around 30 to 40 minutes. As such, by looking only at the charger state in the Bulk Charge state, one cannot tell if the time remaining is 7 hours or 30 minutes.

When the battery voltage reaches the maximum battery voltage permissible, V_overcharge, during the Bulk Charge state as determined at block 610, the charger 230 changes from the Bulk Charge state to the Over Charge state at block 612, where the charge current, I_charge, from the DC/DC converter 526 is set to the overcharge current, I_overcharge. The Over Charge state is a constant voltage mode of operation. In one example, the maximum battery voltage permissible during the Bulk Charge state (i.e., the start of the Over Charge state) is set to 85% of battery charge capacitance, and the end of the Over Charge state the maximum battery voltage permissible is set to 95% of battery charge capacitance.

Once the charging current, I_charge, drops below an overcharge threshold current, I_oct, as determined at block 614, the charger 230 enters the Float Charge state where the charging voltage, V_charge, from the DC/DC converter 526 may be set by the charger controller 520 to a lower floating voltage, V_float, at block 616. The overcharge threshold current, I_oct, may reflect an absorption point in charging the battery 228. That is, once the battery 228 has reached the maximum battery voltage permissible during the Bulk Charge state (i.e., V_overcharge), the current to the battery 228 (and, as a result, the charge rate) is not linear. At the permissible maximum battery voltage, V_overcharge, the current through the battery 228 begins to decline, which marks the beginning of absorption as the charger 230 holds the voltage constant at V_overcharge. This is due to the battery 228 absorbing as much current as it can at this voltage, rather than the charger 230 limiting the charging current, I_charge. The Over Charge state continues at the overcharge voltage, V_overcharge, until the current through the battery declines to a threshold current, I_oct. The overcharge threshold current, I_oct, may represent a steady-state value of a low current that stays constant or declines very little. For example, the overcharge threshold current, I_oct, may be a steady-state current at 5% of battery capacitance or rating, as measured in AHr.

When the charger 230 first enters the Float Charge state, the battery charge is not yet at 100%, but rather a percentage of the final charge. Using the example above where the overcharge threshold current, I_oct, is a steady-state current at 5% of battery capacitance, the start of the Float Charge state indicates about 95% charge with the end of Float Charge state being 100%. Again, because the charge rates and currents are not linear at this stage in the charging cycle, if the current battery charge value (i.e., net AHr in minus net AHr out) does not agree with the transitions from one charge state to another near the end of charge cycle, then the charge indication to the user via the user interface on the display unit 110 may be updated to reflect actual state of charge of the battery as indicated by the charger state transitions, charge current and elapsed time.

The floating voltage, V_float, is the voltage applied to the battery 228 after completion of a charge cycle. This voltage maintains the battery capacity against the effects of self-discharge. In this state, the charger voltage may be temperature-compensated against a loss in battery capacity and/or life expectancy. Further, in this state the battery 228 serves as backup power to the load. If the load current applied during the Float Charge state discharges the battery below 90% of the floating voltage, V_float, as determined at block 618 the charger 230 transitions back to the Bulk Charge state at block 616.

As mentioned above, the modular output power modules 406 are provided within the work platform 102 and convert the DC power (e.g., 20-30 VDC) from the DC power bus 510 to a power output having a different state (e.g., alternating current, a different voltage, etc.). The output power modules 406 include, but are not limited to, one or more alternating current (AC) output power inverters, such as a 120 VAC 150 W output inverter, and/or one or more direct current (DC) output power converters, such as a 19.2 VDC 150 W output converter. Depending on the components the end-user may intend to integrate into the medical cart 100, various combinations of any one or more output power modules may be provided, such as for example, one AC inverter, two AC inverters, one DC converter, two DC converters, or one AC inverter and one DC converter.

Figure 9:
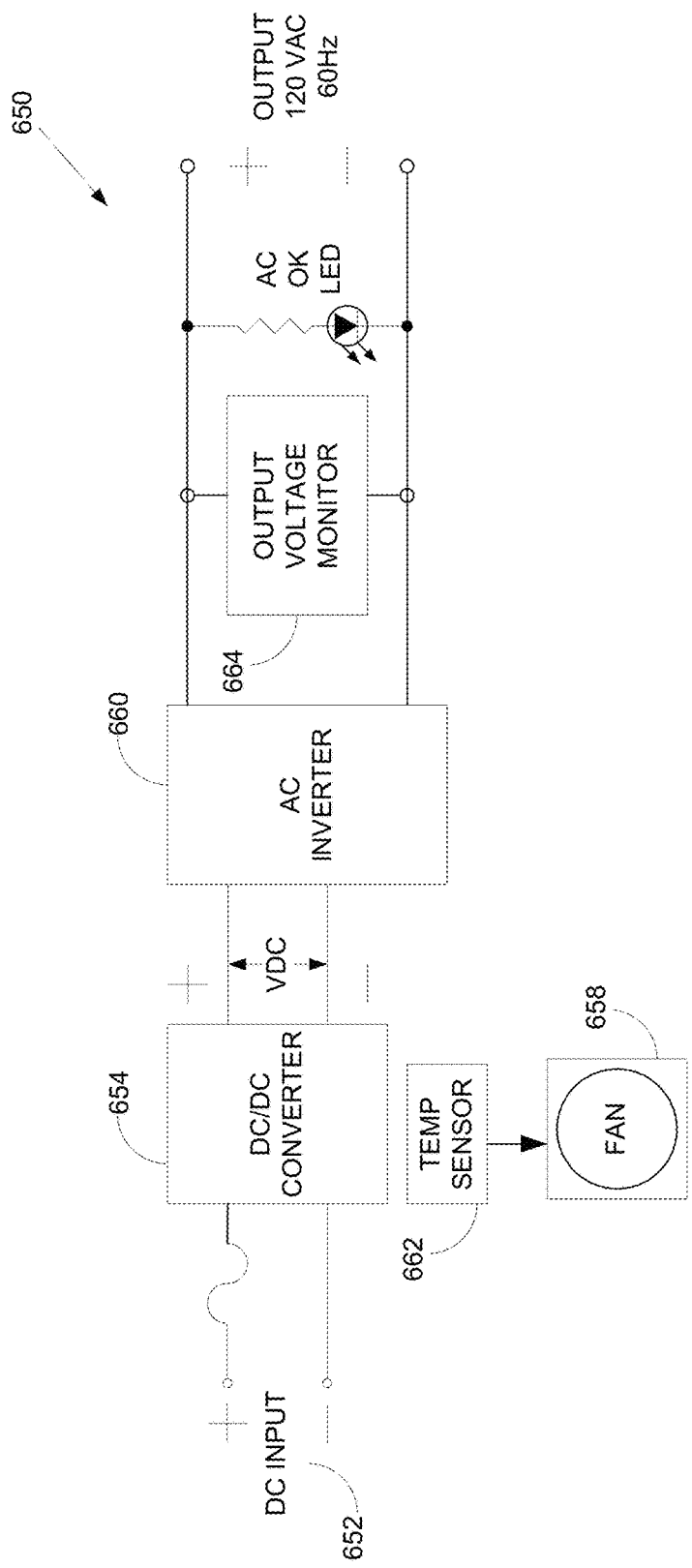
FIG. 9 is an exemplary block diagram of an inverter power module of the medical cart of FIG. 1 in accordance with an embodiment.

An example of an AC inverter output power module 650 is shown in FIG. 9. Input power from the DC power bus 510 is provided (e.g., in the range of 20.0 VDC to 30.0 VDC) to an input 652 of the inverter 650. This input 652 powers a DC/DC converter 654. The DC/DC converter 654 provides power to run a cooling fan 658, which may be a variable speed fan. A temperature sensor 662 in the DC/DC converter 654 monitors the inverter temperature. If the temperature exceeds a particular threshold (e.g., 55° C.), the fan 658 may be switched on or its speed increased. If the temperature exceeds a second threshold (e.g., 75° C.), the AC inverter output power module 650 may be shut down.

The output of the DC/DC converter 654 converts the DC input to a different state (e.g., a different voltage) and powers an AC inverter output 660. The AC inverter output 660 converts the DC/DC converter output voltage into yet another state, namely an alternating current voltage (e.g., 120 VAC, 60 Hz). An output voltage monitoring circuit 664 lights an LED if the output voltage is above approximately a threshold value (e.g., 110 VAC).

Figure 10:
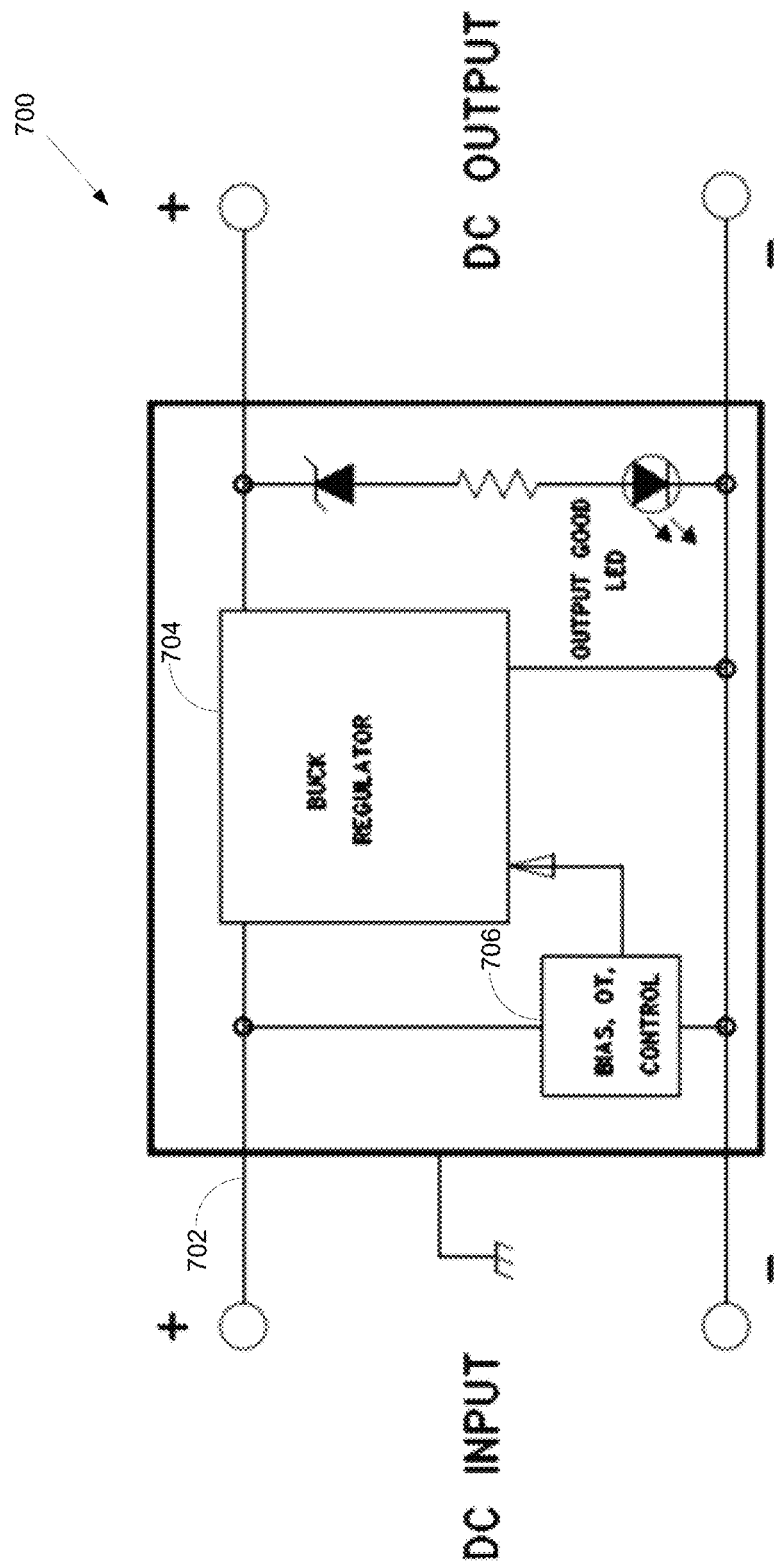
FIG. 10 is an exemplary block diagram of a DC/DC converter power module of the medical cart of FIG. 1 in accordance with an embodiment.

An example of a DC converter output power module 700 is shown in FIG. 10. Input power from the DC power bus 510 (e.g., in the range of 20.0 VDC to 30.0 VDC) is provided to an input 702 of the converter 700. A buck regulator 704 regulates the output voltage to a different direct current voltage (e.g., 19.2 VDC). Internal control circuitry 706 in the DC/DC converter provides a bias voltage to internal circuitry of the regulator 704, over temperature monitoring/ shutdown and an undervoltage lockout function. An LED is lit if the output voltage is above a threshold value (e.g., 18.0 VDC).

The above-disclosed techniques may be implemented using any desired combination of software, firmware and hardware. For example, one or more microprocessors, microcontrollers, application specific integrated circuits (ASICs), etc. may access instructions or data stored on machine or processor accessible storage media to carry out the methods and to implement the apparatus described herein. The storage media may include any combination of devices and/or media such as, for example, solid state storage media including random access memory (RAM), read-only memory (ROM), electrically erasable programmable read-only memory (EEPROM), etc., optical storage media, magnetic storage media, etc.

Thus, while the present disclosure provides specific examples, which are intended to be illustrative only and not to be limiting of the invention, it will be apparent to those of ordinary skill in the art that changes, additions or deletions may be made to the disclosed embodiments without departing from the spirit and scope of the invention.

The invention claimed is:

1. A configurable uninterruptable power system for a medical cart, wherein the medical cart includes a support, a base positioned at a lower end of the support and a work platform positioned at an upper end of the support, the power system comprising:
   a battery positioned within the base of the medical cart and adapted to output direct current electrical power;
   a direct current power bus within the support and electrically coupled to the power supply;
   an electrical output power module positioned vertically above the support and positioned horizontally in front of the support and between a user of the medical cart and the support, said electrical output power module is electrically coupled to the direct current power bus, wherein the electrical output power module is adapted to input the direct current electrical power via the direct current power bus, and further adapted to convert the input direct current electrical power to an electrical power output having a different state; and a charging module removably electrically coupled to the battery and permanently electrically coupled to the electrical output power module, the charging module adapted to either input an alternating current electrical power source and output direct current electrical power to charge the battery or input an alternating current electrical power source and output direct current electrical power to power the electrical output power module without using the battery.

2. The power system of claim 1, wherein the charging module comprises:
- a power module adapted to convert the alternating current electrical power input to a direct current electrical power output;
- a switch operatively coupled to the power module and to the direct current power bus; and
- a controller operatively coupled to the switch and adapted to control the switch to electrically couple the battery to the direct current power bus and adapted to electrically uncouple the battery from the direct current power bus.

3. The power system of claim 2, wherein the controller is adapted to control the switch to electrically couple the battery to the direct current power bus to power the electrical output power module from the battery.

4. The power system of claim 2, wherein the controller is adapted to control the switch to electrically couple the battery to the direct current power bus to power the electrical output power module and/or charge the battery from the alternating current electrical power source.

5. The power system of claim 2, wherein the controller is adapted to control the switch to electrically uncouple the battery from the direct current power bus if the controller detects a fault condition with the battery and/or detects the lack of a battery.

6. The power system of claim 2, wherein the controller is operatively coupled to the power module and further adapted to control the voltage and current of the direct current electrical power output from the power module.

7. The power system of claim 2, wherein the controller is operatively coupled to the battery, and wherein the battery comprises a memory adapted to store battery parameters regarding the battery, and the controller is adapted to read the battery parameters and adapted to control the charge of the battery in accordance with the battery parameters.

8. The power system of claim 2, wherein the power module comprises a temperature sensor and is operatively coupled to the controller, wherein the controller is adapted to receive data regarding the temperature, and to control the switch to electrically uncouple the battery from the direct current power bus if the temperature data exceeds a threshold value.

9. The power system of claim 2, wherein the power module comprises:
- a first electrical power converter adapted to convert the alternating current electrical power input to a direct current electrical power output having a first voltage;
- a second electrical power converter electrically coupled to the first electrical power converter and adapted to input and convert the direct current electrical power output to a direct current electrical power output having a second voltage, wherein the direct current electrical power output having the second voltage comprises the direct current electrical power output from the power module.

10. The power system of claim 1, wherein the electrical output power module comprises an electrical power inverter adapted to convert the direct current electrical power input to an alternating current electrical power output.

11. The power system of claim 1, wherein the input direct current electrical power has a first voltage, and wherein the electrical output power module comprises an electrical power converter adapted to convert the input direct current electrical power to a direct current electrical power output having a second voltage.

12. A medical cart comprising:
- a support comprising a direct current power bus comprising a positive and negative conduction line;
- a work platform positioned at an upper end of the support and comprising an electrical output power module electrically coupled to the direct current power bus, wherein the electrical output power module is adapted to input the direct current electrical power via the direct current power bus, and further adapted to convert the direct current electrical power to an electrical power output having a different state;
- one or more electrical output power modules electrically coupled to the direct current power bus;
- a base positioned at a lower end of the support and comprising a battery electrically coupled to the positive and negative conduction lines of the direct current power bus,
- a charging module electrically coupled to the battery and to the one or more electrical output power modules; and
- a switch positioned between the battery and the direct current power bus and positioned on the negative conduction line.

13. The medical cart of claim 12, wherein the electrical output power modules
comprise:
- an AC inverter adapted to convert the direct current electrical power to alternating current electrical power; and
- a DC/DC converter adapted to convert the direct current electrical power to direct current electrical power of a different voltage.

14. The medical cart of claim 12, which wherein the switch permits the charging module to disconnect from the battery and send power from an alternating current electrical power source to the one or more electrical output power modules.

15. The medical cart of claim 14, wherein the battery comprises a memory adapted to store battery parameters regarding the battery, the power supply further comprising a data communication bus, wherein the charging module is operatively coupled to the memory via the data communication bus.

16. The medical cart of claim 15, wherein charging module is adapted to read the battery parameters, and charge the battery in accordance with the battery parameters.

17. The medical cart of claim 15, wherein the battery parameters comprises one or more of a battery serial number, a battery model number, a battery build date, battery charging parameters and a battery cycle count.

18. The medical cart of claim 12, wherein the controller is operatively coupled to the power module and adapted to:

set the current of the direct current electrical power output to the battery to a first amperage if the voltage of the battery is below a first threshold voltage value;

set the current of the direct current electrical power output to the battery at a second amperage if the voltage of the battery exceeds the first threshold voltage value;

set the current of the direct current electrical power output to the battery to a third amperage if the voltage of the battery exceeds a second threshold voltage value;

set the voltage of the direct current electrical power output to the battery to a first voltage if the current of the direct current electrical power output to the battery is below a first threshold current value; and set the current of the direct current electrical power output to the battery to the third amperage if the voltage of the battery is below a predetermined percentage of the first voltage.

19. The medical cart of claim 12 further comprising:

a direct current output electrically coupled to the direct current power bus and adapted to provide direct current power to a motor which actuates to adjust the height of the work platform.

20. The medical cart of claim 12 further comprising:

a direct current output electrically coupled to the direct current power bus and adapted to provide direct current power to an LED work light.

* * * * *

UNITED STATES PATENT AND TRADEMARK OFFICE
CERTIFICATE OF CORRECTION

| | | |
|---|---|---|
| PATENT NO. | : 9,680,333 B1 | Page 1 of 1 |
| APPLICATION NO. | : 13/840318 | |
| DATED | : June 13, 2017 | |
| INVENTOR(S) | : Richard Jason Brooks and Derek J. Nash | |

It is certified that error appears in the above-identified patent and that said Letters Patent is hereby corrected as shown below:

In the Specification

Column 9, please delete paragraph "FIG. 4 is an exemplary schematic diagram of various.." starting at Line 53 and ending in Column 10, Line 7 and insert it in Column 8 Line 20. The inserted paragraph should be directly above the paragraph starting at Line 20 "The controller 402 embedded within..." and directly below the paragraph starting at Line 10 "FIG. 3 depicts an embodiment of work platform 102...".

Signed and Sealed this
Eighth Day of August, 2017

Joseph Matal
*Performing the Functions and Duties of the*
*Under Secretary of Commerce for Intellectual Property and*
*Director of the United States Patent and Trademark Office*